United States Patent
Michaelsen et al.

(10) Patent No.: US 6,628,748 B2
(45) Date of Patent: Sep. 30, 2003

(54) DEVICE AND METHOD FOR ANALYZING ATOMIC AND/OR MOLECULAR ELEMENTS BY MEANS OF WAVELENGTH DISPERSIVE X-RAY SPECTROMETRIC DEVICES

(75) Inventors: Carsten Michaelsen, Geesthacht (DE); Rüdiger Bormann, Hamburg (DE)

(73) Assignee: GKSS-Forschungszentrum Geesthacht GmbH (DE)

(*) Notice: Subject to any disclaimer, the term of this patent is extended or adjusted under 35 U.S.C. 154(b) by 0 days.

(21) Appl. No.: 10/012,232

(22) Filed: Dec. 7, 2001

(65) Prior Publication Data

US 2003/0103596 A1 Jun. 5, 2003

Related U.S. Application Data

(63) Continuation-in-part of application No. PCT/DE00/01817, filed on Jun. 3, 2000.
(51) Int. Cl.$^7$ .................................................. G41T 1/36
(52) U.S. Cl. ........................ 378/44; 378/84; 252/506; 501/152
(58) Field of Search ...................... 378/44, 73, 82, 378/83, 84, 85; 252/504, 506, 516; 419/14, 20; 501/87, 93, 94, 96.1, 152; 359/838, 850

(56) References Cited

U.S. PATENT DOCUMENTS

| | | | | |
|---|---|---|---|---|
| 4,605,440 A | * | 8/1986 | Halverson et al. | ............. 75/238 |
| 4,661,740 A | * | 4/1987 | Knoch et al. | ........... 313/346 R |
| 5,330,942 A | * | 7/1994 | Holcombe et al. | ............. 501/87 |
| 2003/0026383 A1 | * | 2/2003 | Michaelson et al. | .......... 378/44 |

* cited by examiner

Primary Examiner—Drew A. Dunn
(74) Attorney, Agent, or Firm—Klaus J. Bach

(57) ABSTRACT

In a device and a method for the analysis of atomic and molecular elements by way of wavelength dispersive x-ray spectrometric structures including at least one mirror or focussing device having a multi-layer structure onto which fluorescent radiation generated by primary x-ray or electrons beams from a sample to be examined is directed and the reflected fluorescence radiation is supplied to a measuring device for determining the nature of impurities contained in the sample, the multi-layer structure consists of at least a lanthanum layer and a boron carbide layer.

12 Claims, 2 Drawing Sheets

DEVICE AND METHOD FOR ANALYZING ATOMIC AND/OR MOLECULAR ELEMENTS BY MEANS OF WAVELENGTH DISPERSIVE X-RAY SPECTROMETRIC DEVICES

This is a Continuation-In-Part application of international application PCT/DE00/01817 filed Jun. 3, 2000 and claiming the priority of German application 199 26 056.7 filed Jun. 8, 1999.

BACKGROUND OF THE INVENTION

The invention relates to a device and method for analyzing atomic and/or molecular elements by means of wavelength dispersive x-ray spectrometric devices, comprising at least a mirror or focussing device with multi-layer structures, particularly a device wherein fluorescent radiation induced by incident primary x-rays or electron beams from a sample to be analyzed is directed No a mirror or focussing device before the radiation reaches a measuring or analysis detector.

Such apparatus and methods are used in scientific analyses, but also in the industry for detecting atomic and/or molecular elements in various applications for example for detecting or analyzing very small amounts of impurities or disturbances in a sample. A particularly important area of application in the industrial field is, for example, the examination of semiconductor wafers (silicon wafers, germanium wafers), which form the basis for the manufacture of highly integrated semiconductor circuits.

In this process, x-ray or electron beams of any type are directed onto a sample whereby, as part of the radiation reflected from the sample fluorescent light is emitted. The fluorescent light is generated by the incident x-rays by known physical processes. Before the fluorescent light beam reaches a measuring or analysis arrangement for example in the form of a fluorescence radiation selective detector, it is directed onto a suitable crystal from which it is reflected onto the measurement and analysis detector. The crystals are effective as analyzers. The crystals can be manufactured artificially and may consist of thin alternating layers of two or more materials with different x-ray optical properties. The incident fluorescent light radiation is reflected by these crystals but only that part of the radiation for which the Bragg equation $$n\lambda = 2d \sin \Theta$$

is fulfilled. Herein is $$\lambda \text{ (nm)} = \frac{1.24}{E \text{ (keV)}}$$

wherein n=a natural number (n=1,2,3,4 . . . ); $\lambda$ is the wavelength of the x-radiation; d is the periodicity (lattice parameter) of the analysis crystal; $2\Theta$ is the refraction angle and E is the energy of the x-radiation. If the effects of the refraction are taken into consideration, which effects are very small for x-radiation, a modified equation is obtained from which the wavelength of the reflected x-radiation can be determined with the giver, angles $\Theta$ and the lattice parameter d of the analyzer based on the first equation or, respectively, the modification thereof. With a variation of the angle, the wavelength of the reflected rays can be selected in a controlled manner.

The advantage of the artificial crystals which, consisting of many uniformly changing layers—so-called multi-layer structures, is that the materials of the multi-layer can be selected so as to optimize the operation. This is an important advantage of the artificially manufactured multi-layer structures as compared to material crystals.

The intensity of the reflected light depends to a large degree on the material used for the multi-layer structures. It is also possible to vary the lattice parameters within wider limits as it is possible with natural crystals.

It is therefore a particular advantage of the multi-layer structure acting as an analyzing device that the analysis of light elements is facilitated with a uniform intensity and without unhealthy side effects. This is an additional advantage when compared with natural crystals, if natural crystals can be used at all for the analysis of light elements.

So far the multi-layer structure or, respectively, the individual layers of the multi-layer structure has been adjusted to the atomic or molecular element that was expected from the sample being examined. Of high importance in the semiconductor industry is, for example, the determination of the boron content in oxygen-containing materials such as boron phosphorus silicate since this material is generally used during the manufacture of microelectronic components.

So far, a multi-layer structure of molybdenum boron carbide layers has been used for the detection of boron. Such a layer is for example described in U.S. Pat. No. 4,785,470.

Such a molybdenum boron carbide multi-layer and the tungsten carbon multi-layers, which have been used for that purpose, have in the energy range of 183 V only a reflectivity of about 35.4% or, respectively, 10% at an optimal angle of $\Theta=26.5°$ (with a tungsten carbon multi-layer structure). Furthermore, the use of tungsten carbon multi-layer structures for the detection of boron in samples, which also contain oxygen, has been found problematic. This is essentially because the emission line of oxygen with a value of E=525 eV has essentially three times the energy of the emission line of boron with E=83 eV. Accordingly, the multi-layer structure reflects in accordance with the equation given earlier, the oxygen line in the third Bragg order (n=3) at about the same angle as the boron line in the first Bragg order (n=1). Since the earlier referred to tungsten-carbon multi-layer has for E=525 eV at $\Theta=26.7°$ in the third order still a reflectivity of 0.24%, a wavelength dispersive separation of the boron and oxygen lines and, consequently, a clear detection of the two elements is insufficient with this multi-layer if at all possible.

The result is improved if molybdenum-boron carbide multi-layers (Mo—$B_4C$) are used as they are for an optimum detection of boron in commercial x-ray fluorescence spectrometers. In comparison with a W—C multi-layer a clearly increased reflectivity of 35.4% in the first Bragg order is achieved. At the same time, the reflectivity of such a Mo—$B_4C$ multi-layer for 525 eV in the third Bragg order is reduced to 0.16% so that the oxygen line is somewhat suppressed.

It is however a disadvantage that W—C— as well as Mo—$B_4C$ multi-layers have also a significant reflectivity for E=90 eV. This is also very important for the semiconductor industry since the silicon-L-emission lines are about at 90 eV. Computations reveal that a Mo—$B_4C$ multi-layer with d=8 nm at an angle of $\Theta=25.9°$ have, in addition to the desirable high reflectivity at E=183 eV for the optimal detection of boron, also an undesirable reflectivity of about 3.2° at E=90 eV. This results with boron-containing samples such as boron phosphor silicate (BPSG) disposed on silicon wafers in an increased background signal which is disadvantageous for the x-ray spectrometric detection limit of boron.

It is the object of the present invention to provide a device and method for an improved x-ray analysis for the detection of boron wherein the device and the method can utilize known means and procedures so that available analysis equipment can essentially be continued to be used and the equipment can be easily and inexpensively installed and operated in research laboratories and industrial plants.

SUMMARY OF THE INVENTION

In a device and a method for the analysis of atomic and molecular elements by way of wavelength dispersive x-ray spectrometric structures including at least one mirror or focussing device having a multi-layer structure onto which fluorescent radiation generated by primary x-ray or electrons beams from a sample to be examined is directed and the reflected fluorescence radiation is supplied to a measuring device for determining the nature of impurities contained in the sample, the multi-layer structure consists of at least a lanthanum layer and a boron carbide layer.

With the device according to the invention, the detection of boron is greatly facilitated particularly in the energy range of 180 eV. The particularly favorable x-ray optical properties of the materials forming the layer pairs such as lanthanum and boron carbide provide, in comparison with the earlier mentioned known analyses, for an increased reflectivity for the boron line as well as a substantially improved suppression of the oxygen-K— as well as the silicon-L-lines.

The multi-layer structure consisting of the base layer pars lanthanum and boron carbide has for the boron line a reflectivity of 60% in the first Bragg order. This is almost twice the value obtained by the best analyzers known up to now. Furthermore, the reflectivity for 90 eV is only 0.65% so that the suppression of the Si-L-line with respect to the earlier solutions is improved by the factor 5. At the same time, at 525 eV, the reflectivity is only 0.016% so that the suppression of the oxygen line is improved by more than a factor 10 over the best results obtained with the best multi-layer structure analyzers presently in use.

The sum of all these factors results in a substantially improved signal-noise ratio and, consequently in a substantial improvement in the x-ray spectrometric detection limits particularly for boron.

In a particularly advantageous embodiment, the multi-layer structure consists of a number of 1 to 100 layer pairs, that is, of 2–200 individual layers. The number of layers or, respectively, layer pairs, which are selected for the formation of a particular multi-layer structure depends essentially on the desired analysis or respectively, measuring task and the expected type and amount of impurities in the sample to be examined.

It is particularly advantageous if the multi-layer structure consists of a number of 40 to 50 layer pairs, that is, of 80 to 100 individual layers.

In a basic version of the device, the thickness of each multi-layer structure is constant; but it is also possible to provide in each multi-layer pair layers with different thickness.

In the embodiments described above, it is basically made sure that a parallel fluorescence beam is reflected over the whole surface of the multi-layer structure with maximum intensity.

In another advantageous embodiment, the thickness of the respective multi-layer structure varies over the area thereof as far as it can be made sure that parallel fluorescence rays, which reach the multi-layer structure under different angles, are reflected over the whole surface area of the multi-layer structure with maximal intensity. The variation of the incident angles $\Theta$ is compensated for by a variation of the lattice parameter d in accordance with the earlier referred to equation or the computation-corrected modification thereof so that $\lambda$ remains constant.

Preferably, the device is so modified that the multi-layer structure is curved. In another advantageous embodiment, she multi-layer structure is disposed on a substrate. However in all embodiments, the multi-layer structure may be disposed on a substrate. It can be made sure in this way that a non-parallel fluorescence beam, which reaches the multi-layer structure at different locations at different incident angles, can be transformed in its beam shape so that for example a divergent fluorescent light beam reaching the multi-layer structure becomes a parallel or a focussed fluorescent light beam. It may also be advantageous to provide for different thicknesses of the individual layers of the multi-layer structure, that is, to modify the thickness of a layer over the extent of the layer so that the multi-layer structure reflects the desired wave length of the fluorescent radiation reaching the multi-layer structure under different incident angles over the surface with maximum intensity.

The multi-layer structure may also have layer arrangements wherein one of a pair of layers has a uniform thickness whereas the other of the pair of layers is of varying thickness.

Preferably, the thickness of the layer is in the area of 1 to 20 nm. Tests have shown that, with those thicknesses, the highest reflectivity and resolution can be obtained for the multi-layer structure.

The method for the analysis of atomic and/or molecular elements by means of wavelength dispersive x-ray spectroscopic devices including a mirror and focussing arrangement with at least one multi-layer structure onto which the primary x-ray or fluorescence rays are directed in such a way that induced fluorescent light generated by a sample as a result of primary x-ray or electron beams directed to a mirror or focussing arrangement before reaching a measuring or analysis detector is characterized in that the primary x-rays or the fluorescent light is directed to a multi-layer structure consisting of at least a layer pair of lanthanum (La layer) and a boron carbide layer ($B_4C$ layer).

With the method according to the invention, a reflectivity of over 60% in the first Bragg order can be reached for the boron line. This is almost twice the value reached by the best of today's methods in which multi-layer structures are employed as analyzers.

Generally, the advantages as listed for the device according to the invention are also provided by the method according to the invention.

The invention will be described below gun greater detail on the basis of an embodiment with reference to the accompanying drawings.

DESCRIPTION OF A PREFERRED EMBODIMENT

Figure 1:
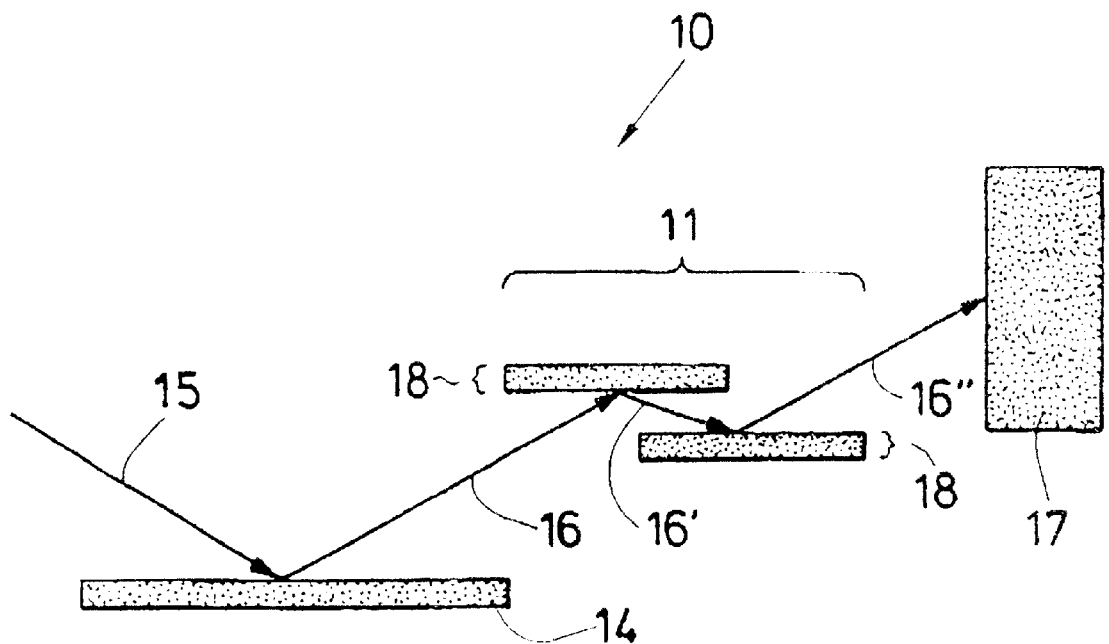
FIG. 1 shows the path of an x-ray beam provided by an x-ray source to a sample and from the sample to two multi-layer structures and then to a measuring or analysis device (detector).

First, reference is made to FIG. 1, which shows schematically a device 10 for the analysis of atomic and/or molecular elements as it may be used with minor modifications for many applications.

From an x-ray or electron source, which is not shown in the figures, primary x-rays or electron beams 15 are omitted and directed onto a sample 14, which is for example a silicon wafer, in order to detect impurities on the surface and in the area close to the surface of the silicon wafer. By well-known physical processes fluorescent beams 16 are generated as reflected beams which, in their radiation continuous spectrum include information concerning the type of additional atomic and/or molecular elements contained in the silicon wafer or, respectively, the sample 14. The fluorescence rays 16 are directed onto a mirror- or focussing device 11, which is formed in the example of FIG. 1 by two mirror or focussing arrangements 11 of which each comprises a multi-layer structure 12. In another embodiment of the device 10 only a single mirror or focussing arrangement may be provided. The fluorescence rays 16', 16' reflected from the focussing device 11 are directed onto a measuring or analysis structure (detector) 17 by means of which quantitative and qualitative indications concerning the type of the atomic and/or molecular elements in the material of the sample 14 can be obtained in a known manner.

Figure 2:
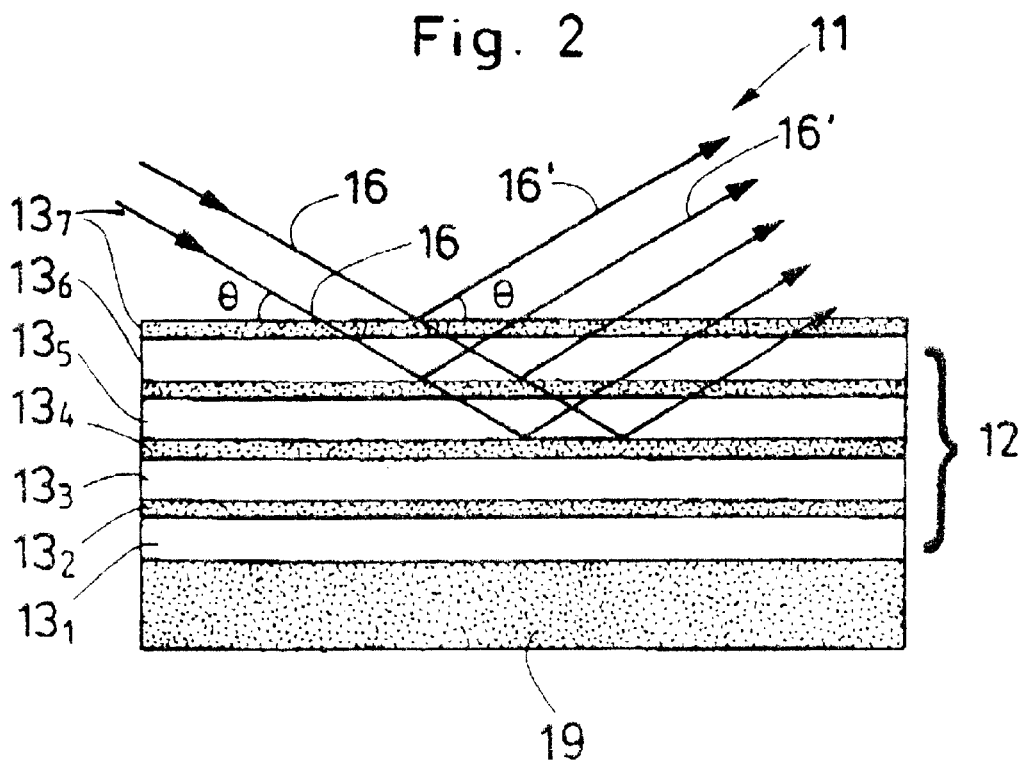
FIG. 2 shows the path of incident and reflected rays (here for the example of fluorescence rays) with a multi-layer structure which is disposed on a substrate.

FIG. 2 shows for example a section of the mirror and/or focussing structure 11, which represents the actual multi-layer structure 12 which, in the example of FIG. 2, is disposed on a substrate 19.

The individual layers $13_1 \ldots _n$ form, with all the pairs $13_1$; $13_2$, $13_3$; $13_4$, $13_5$; $13_5$; $13_6$; etc. the complete multi-layer structure 12. Each of the layers of each pair of layers is formed by a La-layer and a $B_4C$ layer. The incident beam, in the example fluorescence radiation 16, is reflected at each interface area of a layer pair and leaves the mirror or focussing device 11 as reflected rays 16'. The rays 16' are then directed either onto a second mirror or focussing device 11 (see FIG. 1) and from there to a measuring or analysis device 17 or they are directed immediately to a measuring or analysis device 17 without repeated reflection by a mirror- or focussing structure 11.

Figure 3:
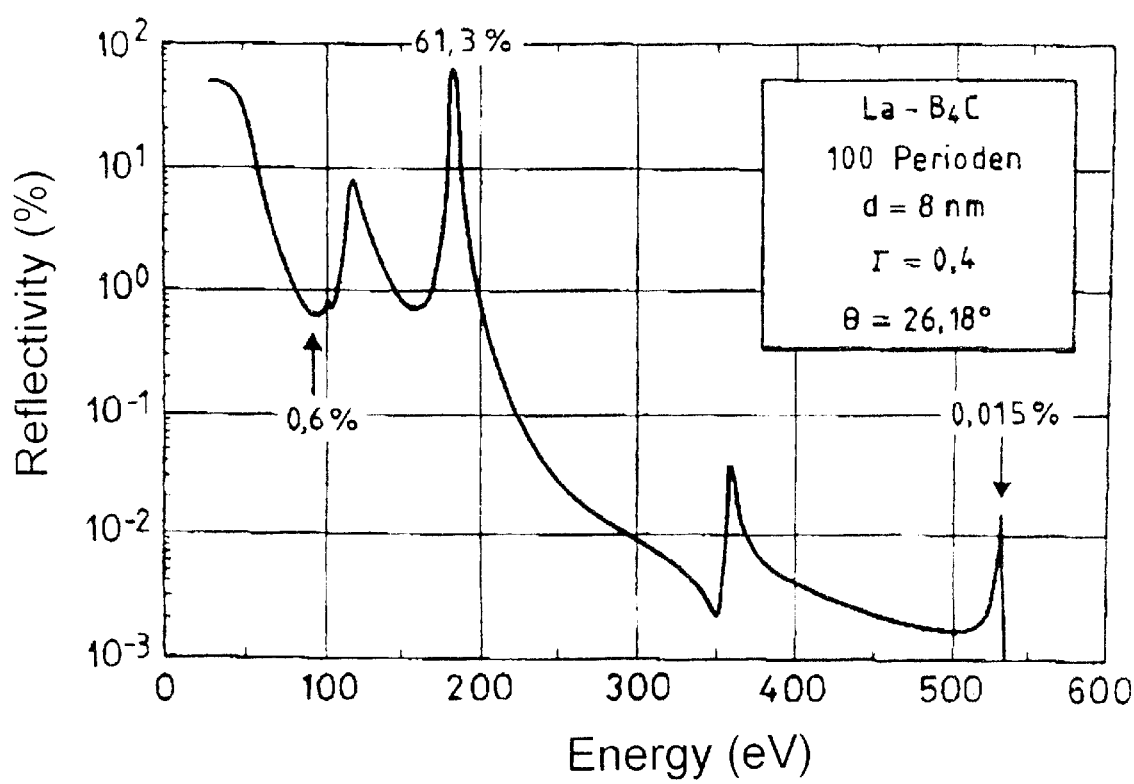
FIG. 3 shows a graphic representation of the reflectivity of a La—$B_4C$ multi-layer structure consisting of 100 periods with d=8 nm and a layer thickness ratio Γ=0.4, at an angle of Θ=26.18° as a function of the energy.

FIG. 3 shows in combination with the table below that, as mentioned already earlier, the multi-layer (La—$B_4C$ multi-layer) has for the boron line a reflectivity of more than 60%. This is almost twice the value obtained with the best multi-layer structures used presently in connection with analyses. Furthermore, the reflectivity for 90 eV is only 0.65% so that also the suppression of the Si—L line is improved by a factor of 5 when compared with prior art solutions. Furthermore, the reflectivity at 525 eV is only 0.016%, whereby the suppression of the oxygen line improved by a factor of 10 in comparison with the best presently used analyses. With all these factors, a substantially improved signal-to-noise ratio is obtained whereby the x-ray spectrometric detection limit is substantially improved, especially for boron.

| Analyzer | Reflectivity at v 90 eV (%) | Reflectivity at v 183 eV (%) | Reflectivity at 525 eV (%) |
|---|---|---|---|
| W-C | 3.6 | 10.4 | 0.24 |
| Mo-$B_4C$ | 3.2 | 35.4 | 0.18 |
| La-$B_4C$ | 0.65 | 61.3 | 0.016 |

The measuring procedure is performed in accordance with the beam path arrangement as described above in connection with the representation of FIG. 1, which shows the device according to the invention in an exemplary manner. The beams or rays are generated by an x-ray or electron beam source, which is not shown, and are directed to a measuring or analysis apparatus (detector) 17.

What is claimed is:

1. A device for the analysis of atomic and molecular elements by way of wavelength dispersive, x-ray spectrometric structures, comprising at least one mirror or focussing device including a multi-layer structure, onto which fluorescence radiation generated by primary x-rays or electron beams from a sample to be examined is directed, said multi-layer structure consisting of at least a lanthanum layer (La layer) and a boron-carbide layer ($B_4C$ layer) forming a layer pair.

2. A device according to claim 1, wherein said multi-layer structure comprises 1 to 100 layer pairs.

3. A device according to claim 1, wherein said multi-layer structure comprises 40 to 50 layer pairs.

4. A device according to claim 1, wherein each multi-layer structure has a uniform thickness.

5. A device according to claim 1, wherein the thickness of the multi-layer structure varies.

6. A device according to claim 1, wherein said multi-layer structure is curved.

7. A device according to claim 1, wherein said multi-layer structure is disposed on a substrate.

8. A device according to claim 7, wherein said substrate is curved.

9. A device according to claim 1, wherein individual layers of the multi-layer structure have all the same thickness.

10. A device according to claim 1, wherein the individual layers of the multi-layer structure have different thicknesses.

11. A device according to claim 1, wherein the individual layers of said multi-layer structure have each a thickness of to 20 μm.

12. A method for the analysis of atomic and molecular elements by way of wavelength dispersive x-ray spectrometric structures comprising at least one mirror or focussing device consisting of at least a lanthanum layer and a boron carbide layer forming a multi-layer structure, said method comprising the steps of directing primary x-ray or electron beams onto a sample to be examined to cause it to emit fluorescence radiation, directing said fluorescence radiation onto said multi-layer structure so as to cause its reflection therefrom and directing the reflected fluorescence radiation to a measuring device for determining the nature of impurities contained in said sample.

* * * * *